US012558459B2

(12) United States Patent
Monroe

(10) Patent No.: US 12,558,459 B2
(45) Date of Patent: Feb. 24, 2026

(54) SHAPE MEMORY POLYMER HYDROGELS FOR WOUND HEALING

(71) Applicant: Mary Beth Monroe, Syracuse, NY (US)

(72) Inventor: Mary Beth Monroe, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 916 days.

(21) Appl. No.: 17/606,657

(22) PCT Filed: Apr. 30, 2020

(86) PCT No.: PCT/US2020/030592
§ 371 (c)(1),
(2) Date: Oct. 26, 2021

(87) PCT Pub. No.: WO2020/226983
PCT Pub. Date: Nov. 12, 2020

(65) Prior Publication Data
US 2022/0211913 A1 Jul. 7, 2022

Related U.S. Application Data

(60) Provisional application No. 62/842,728, filed on May 3, 2019.

(51) Int. Cl.
*A61L 27/52* (2006.01)
*A61L 27/48* (2006.01)
*A61L 27/54* (2006.01)
*A61L 27/56* (2006.01)
*A61L 27/58* (2006.01)

(52) U.S. Cl.
CPC .............. *A61L 27/52* (2013.01); *A61L 27/48* (2013.01); *A61L 27/54* (2013.01); *A61L 27/56* (2013.01); *A61L 27/58* (2013.01); *A61L*

2300/404 (2013.01); *A61L 2300/426* (2013.01); *A61L 2300/622* (2013.01)

(58) Field of Classification Search
CPC .......... A61L 27/52; A61L 27/48; A61L 27/54; A61L 27/56; A61L 27/58; A61L 2300/404; A61L 2300/426; A61L 2300/622; A61L 27/18; A61L 27/50; C08G 18/4244; C08G 18/664; C08G 18/6644; C08G 18/6677; C08G 2210/00; C08G 18/3212; C08G 18/3275; C08G 18/5024; C08G 18/6655; C08G 18/6688; C08G 18/4833; C08G 18/10; C08G 18/6674; C08G 18/73
See application file for complete search history.

(56) References Cited

U.S. PATENT DOCUMENTS

| | | | | |
|---|---|---|---|---|
| 2011/0052694 A1* | 3/2011 | Stinchcomb | ......... | A61K 31/222 |
| | | | | 514/420 |
| 2018/0085489 A1* | 3/2018 | Hanson | .................. | A61K 47/34 |

* cited by examiner

*Primary Examiner* — Frederick F Krass
*Assistant Examiner* — Abdulrahman Abbas
(74) *Attorney, Agent, or Firm* — David L. Nocilly; Bond, Schoeneck & King PLLC

(57) ABSTRACT

A shape memory polymer hydrogel that is biodegradable, includes antimicrobial agents, and has a tunable drug delivery is used for wound healing internally and externally. The shape memory polymer is synthesized using a combination of hydrophilic precursors that are configured to have two to four functional end groups, with at least one component that has at least three functional groups. The synthesis route provides for a covalently crosslinked thermoset hydrogel. The chemistry can be tuned to provide desired transition temperatures for delivery (e.g. below 37° C.) and desired pore sizes for healing (e.g. 250-500 μm).

18 Claims, 9 Drawing Sheets

Specification includes a Sequence Listing.

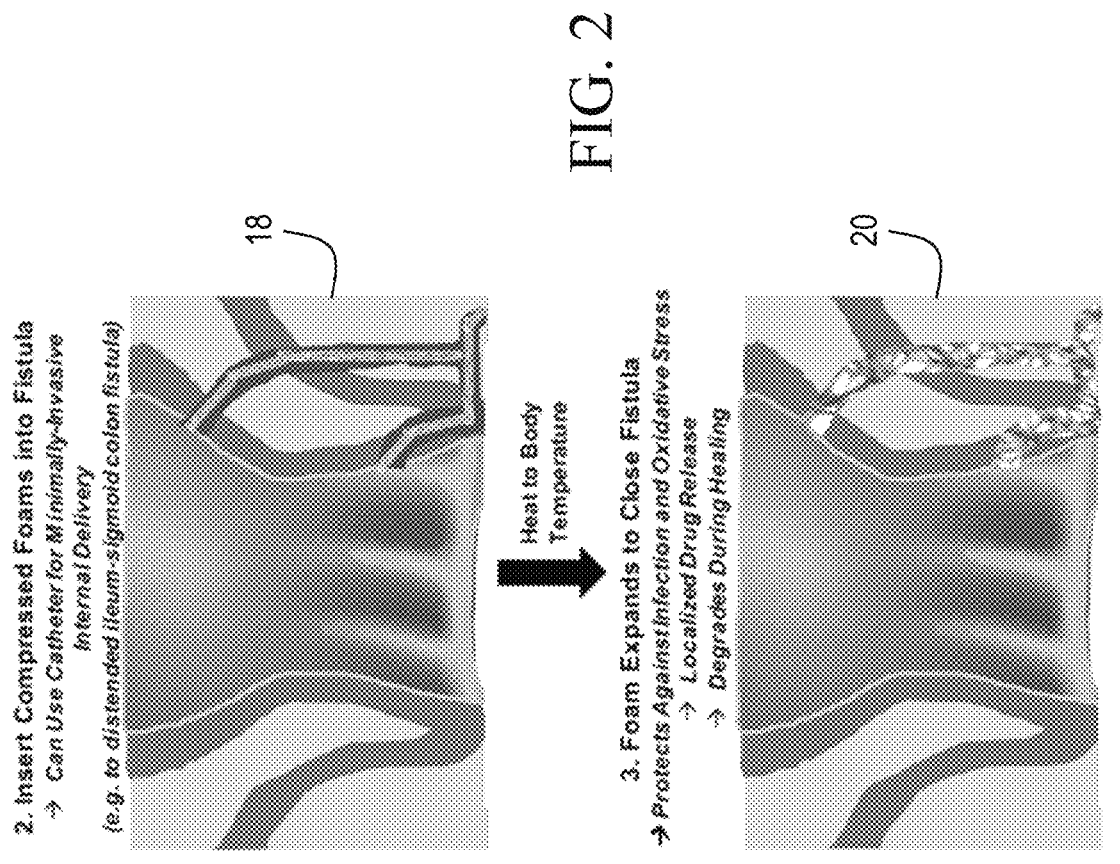

2. Insert Compressed Foams into Fistula
→ Can Use Catheter for Minimally-Invasive Internal Delivery
(e.g. to distended ileum-sigmoid colon fistula)

Heat to Body Temperature

3. Foam Expands to Close Fistula
→ Protects Against Infection and Oxidative Stress
→ Localized Drug Release
→ Degrades During Healing

FIG. 2

SHAPE MEMORY POLYMER HYDROGELS FOR WOUND HEALING

CROSS-REFERENCE TO RELATED APPLICATIONS

The present application claims priority to U.S. Provisional No. 62/842,728, filed on May 3, 2019.

BACKGROUND OF THE INVENTION

1. Field of the Invention

The present invention is related to wound healing systems and, more specifically, to a shape memory polymer hydrogel that is degradable and that can release antimicrobial agents.

2. Description of the Related Art

Chronic wounds, such as diabetic ulcers, fistulas, and pressure sores, are a global healthcare problem, affecting ~5.7 million patients per year in the United States alone. They represent a significant financial burden to patients and healthcare providers; healing one diabetic ulcer is estimated to cost $50,000. Crohn's disease, along with other types of irritable bowel disease (IBD), surgical complications, cancer, and childbirth, can lead to fistula formation between portions of the urinary, reproductive, and digestive systems, essentially creating internal chronic wounds. While new research has focused on providing dressing options for healing chronic wounds, they still account for up to 70% of foot amputations. Thus, an improved chronic wound dressing is required to improve patient outcomes. There are numerous benefits of moist wound dressings in healing and infection prevention. Therefore, a number of hydrogel-based wound dressings have been developed to address this problem.

Traditional hydrogel slabs are limited in their ability to conform to irregularly-shaped wounds, which can hinder healing processes. To address this issue, researchers have developed injectable dressings from microparticles or in situ crosslinkable systems; however, these systems often either fail to match the mechanical properties of native tissue or lack an interconnected porous structure, both of which are important for effective healing.

Additionally, infection remains a significant concern in chronic wounds, and antibiotic resistant bacterial strains make treating infections more difficult. Silver is frequently employed as an antimicrobial in current research, but its safety and efficacy results are inconsistent, and it presents an environmental concern.

Dressing changes cause pain and increased infection risks, making a degradable option that can be left in place throughout healing desirable. Current research on degradable dressings is limited by the need for biocompatible degradation byproducts that do not hinder the healing process.

BRIEF SUMMARY OF THE INVENTION

The present invention comprises shape memory polymer hydrogels that can be used for wound healing. In a first embodiment, the present invention is porous wound scaffold comprising a shape memory polymer foam comprised of a polymerized multi-armed precursor and an antimicrobial compound. The shape memory polymer foam will exhibit a transition from a first geometry to a second geometry in response a predetermined temperature. The antimicrobial compound may be pendant to the multi-armed precursor. The antimicrobial compound may also be copolymerized with the multi-armed precursor. The polymerized multi-armed precursor may be poly(ethylene glycol). The antimicrobial compound may be a plant-based phenolic acid. The transition temperature is preferably below 37° C. The shape memory polymer foam should have an average of pore size of between 250 and 500 μm.

In another embodiment, the present invention is a porous wound scaffold, comprising a shape memory polymer foam comprised of a polymerized multi-armed precursor and a degradable compound. The shape memory polymer foam will exhibit a transition from a first geometry to a second geometry in response a predetermined temperature. The degradable compound may be pendant to the multi-armed precursor. The degradable compound may be copolymerized with the multi-armed precursor. The polymerized multi-armed precursor may be poly(ethylene glycol). The degradable compound may comprise SEQ ID NO: 1. The porous wound scaffold of claim 12, wherein the transition temperature is below 37° C. The transition temperature is preferably below 37° C. The shape memory polymer foam should have an average of pore size of between 250 and 500 μm.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 2 is a schematic of the shape memory properties and proposed application of shape memory polymer hydrogel foams in an internal wound bed;

DETAILED DESCRIPTION OF THE INVENTION

Figure 1:
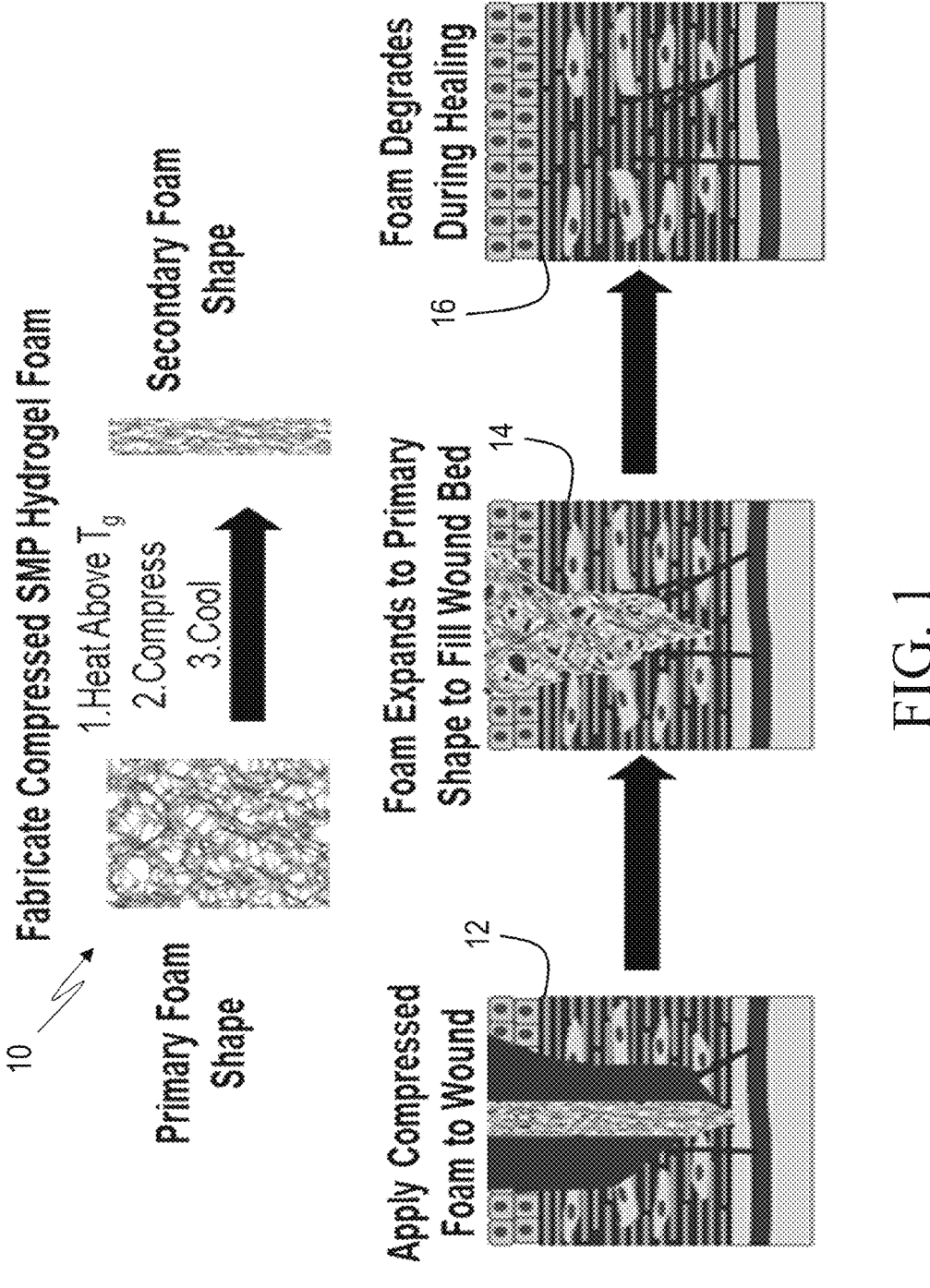
FIG. 1 is a schematic of the shape memory properties and proposed application of shape memory polymer hydrogel foams in an external wound bed.

Referring to the figures, wherein like numerals refer to like parts throughout, there is seen in FIG. 1 a schematic representation of a shape memory polymer (SMP) hydrogel foam 10 for chronic wound healing that is antimicrobial and degradable. SMP foams are porous materials that can be heated and compressed into a low-profile geometry, which is retained after cooling. This shape enables minimally invasive delivery of SMP foams. Once the compressed foams are placed into a wound bed 12, they are heated to body temperature and expand back to their original shape 14 to conform to the wound geometry, as seen in FIGS. 1 and 2, to provide a moist, shape-filling scaffold. The porous morphology allows for cellular ingrowth and new blood vessel formation. Foam pore sizes should be between 250 and 500 μm, to enable cell migration into the foam. The transition temperature should be below 37° C. to enable actuation after application to the body. Foam 10 will degrade during the healing process 16 so that the result is just healed tissue. Referring to FIG. 2, foam 10 may also be used for internal wounds, such as a fistula 18 so that expansion of foam in situ closes the fistula 20. Foam 10 will protect against infections and oxidative stress, may be used for localized drug release, and will degrade during healing to leave only healed tissue in place.

The polymer system of the present invention can be modified to be antimicrobial, degradable, and/or capable of local drug delivery. The shape memory polymers may be synthesized using a combination of hydrophilic precursors, including, but not limited to, poly(ethylene glycol) (PEG) or poly(vinyl alcohol). These precursors are configured to have two or more functional endgroups, with at least one component that has at least three functional groups. Functional groups may include isocyanates and amines; hydroxyl linkages may be employed in addition to amines. The synthesis route provides for a covalently crosslinked thermoset hydrogel.

Shape memory properties are based upon the glass transition temperature (Tg) and/or the melting temperature (Tm) of the polymer network, which is dependent upon hydrogen bonds between urea (and urethane, if hydroxyl-terminated monomers are used) linkages on adjacent chains. The hydrophilic precursors will absorb water to aid in healing. Compressible foams may be fabricated using standard polyurethane blowing processes with the addition of chemical (e.g. water) and/or physical blowing agents. For example, an isocyanate-containing pre-polymer made be synthesized and mixed with a hydroxyl/amine-containing monomer mix. The two mixtures are then exposure to water as a chemical blowing agent and heated to form 3D porous foams. Alternatively, a particulate leaching techniques may be used to form foams (e.g. polymerize SMP monomers around salt or dissolvable microparticles, then wash out the small particles to leave behind pores). Bulk scaffolds may be synthesized without blowing agents and can be modified to provide smaller particles of varied sizes to fill wounds. Fibers may be fabricated using in situ crosslinking of precursors in a standard fibrous scaffold fabrication set up, including, but not limited to electrospinning. Scaffolds according to the present invention can be used to heal a range of tissue wounds, including, but not limited to dermal wounds and surgical wounds.

The chemistry of the present invention can be tuned to provide antimicrobial properties via covalent modification with monomers that include, but are not limited to, traditional antibiotics, naturally occurring small molecules with antimicrobial efficacy, and/or antimicrobial peptides. Antimicrobials can be incorporated directly as hydrogel monomer or via prior modification of a hydrogel precursor.

The present invention may include, but not be limited to, hydrolytically-degradable esters, oxidatively-degradable ethers, and/or enzymatically-degradable peptides and/or monomers to incorporate degradable linkages. Degradable linkages can be directly incorporated as hydrogel monomers or incorporated via prior modification of a hydrogel precursor.

The system will be further built upon by the incorporation of a tunable drug delivery system. A model immunosuppressant drug may be e incorporated into microspheres within the foams to provide tunable release profiles throughout the foam degradation process.

Figure 3:
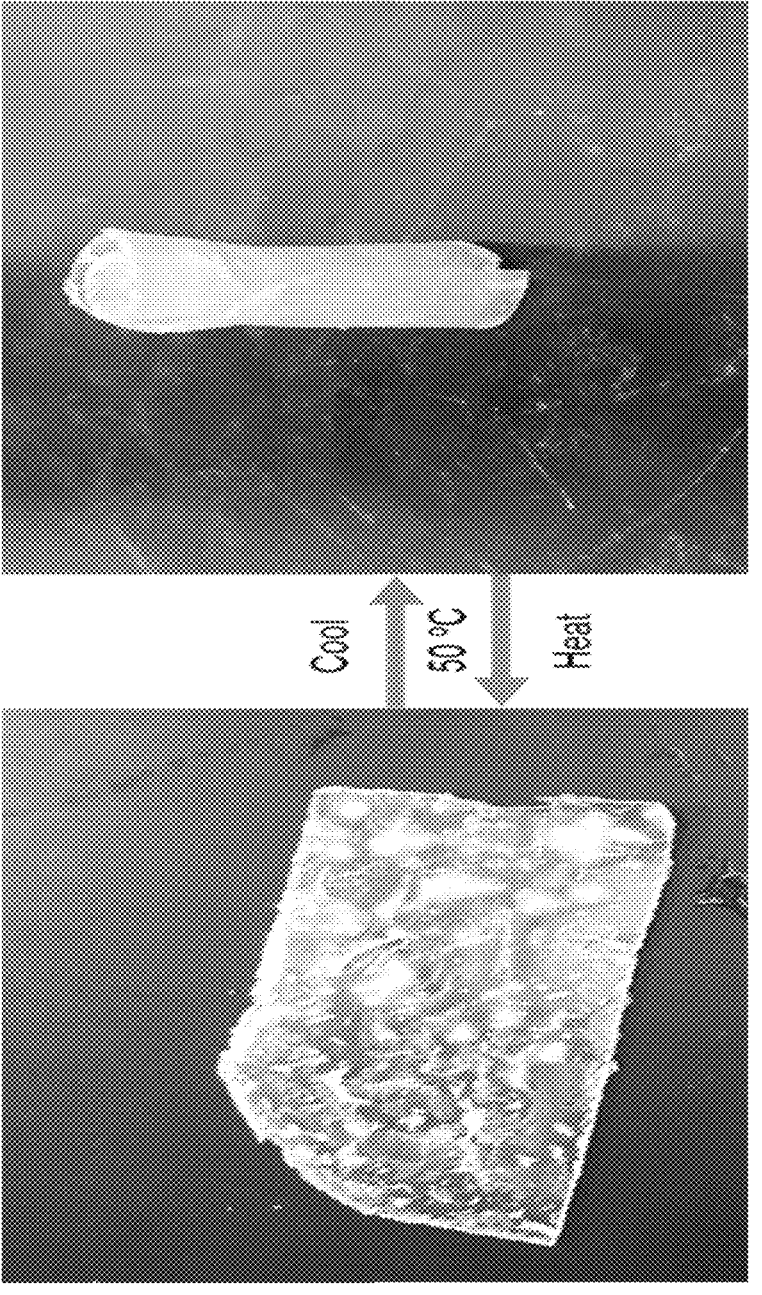
FIG. 3 is a perspective view of an example of the shape memory polymer hydrogel in the first shape and second shape.

As seen in FIG. 3, the SMP hydrogel foam has a primary shape that is set during synthesis. When the SMP hydrogel foam is heated to the transition temperature, the SMP can be deformed a temporary second shape that is fixed upon cooling. The SMP hydrogel foam will remain in the second shape when below transition temperature. In use, the SMP hydrogel foam in the second shape can be placed into a wound bed, where it would be heated up above the transition temperature. Once above the transition temperature, the SMP hydrogel foam will expand to the first shape and conform to the wound geometry.

Figure 4:
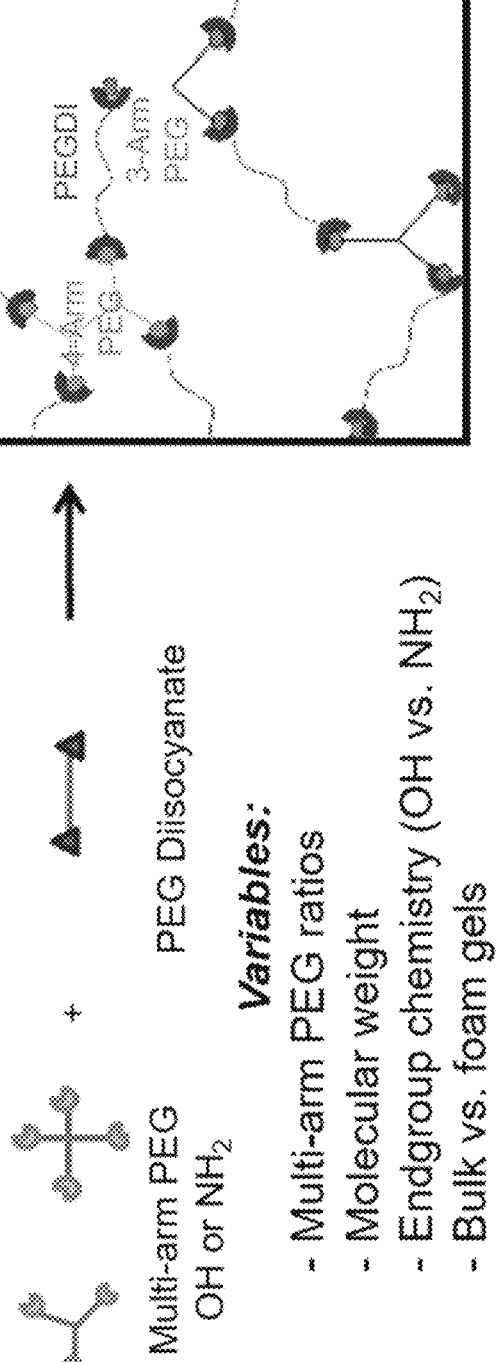
FIG. 4 is a schematic of a synthesis process for a shape memory polymer hydrogel wound scaffold according to the present invention.
Figure 5:
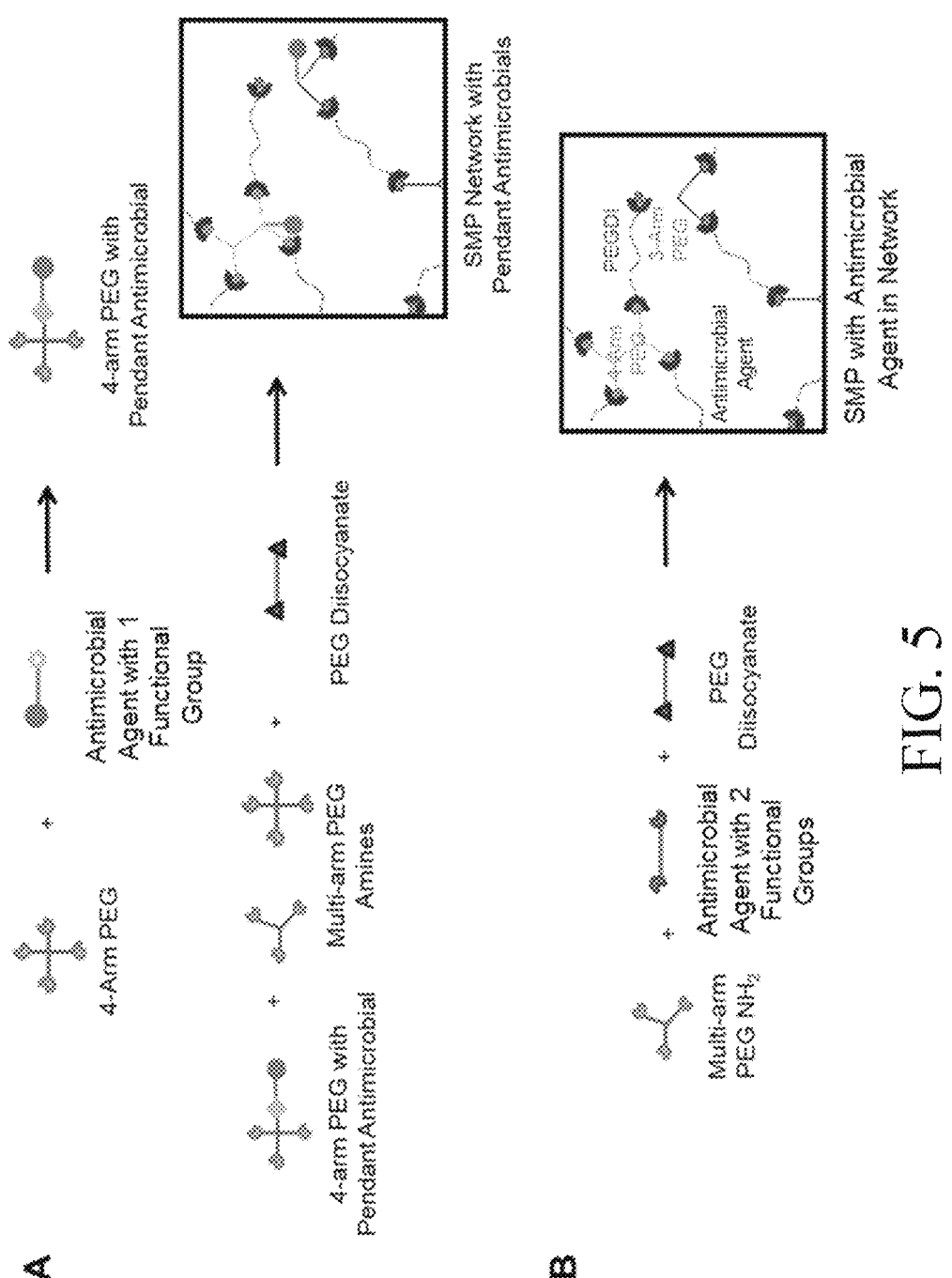
FIG. 5 is a schematic of two synthesis processes for two potential routes (A: Prior modification of monomer with an antimicrobial agent with one functional group and B: Direct incorporation of an antimicrobial agent with two functional groups) for incorporating antimicrobial compounds into a shape memory polymer hydrogel wound scaffold according to the present invention.

There is shown in FIG. 4 a schematic of a synthesis process for a shape memory polymer hydrogel wound scaffold according to the present invention. Multi-arm PEGs (hydroxyl (OH) or amine (NH2) endgroups) and PEG diisocyanates may be reacted together to form a hydrophilic, chemically crosslinked network Hydrophilic foams will provide a moist healing environment, and this platform material can be built upon by the introduction of antimicrobial groups, as seen in FIG. 5, to reduce infection risks than can hinder healing. Antimicrobial monomers could be synthesized via a reaction between antimicrobial agents with one functional group (e.g. phenolic acids) and 4-arm PEG OH to make a triol with a pendant antimicrobial. According to the method outlined in FIG. 5B, antimicrobial agents with two functional groups (e.g. peptides) could be incorporated into foams via reactions between amine groups and PEG diisocyanate. Following synthesis of antimicrobial SMPs, they may be characterized in terms of antimicrobial efficacy against clinical isolates from infected wounds and cytocompatibility with relevant cell types.

Figure 6:
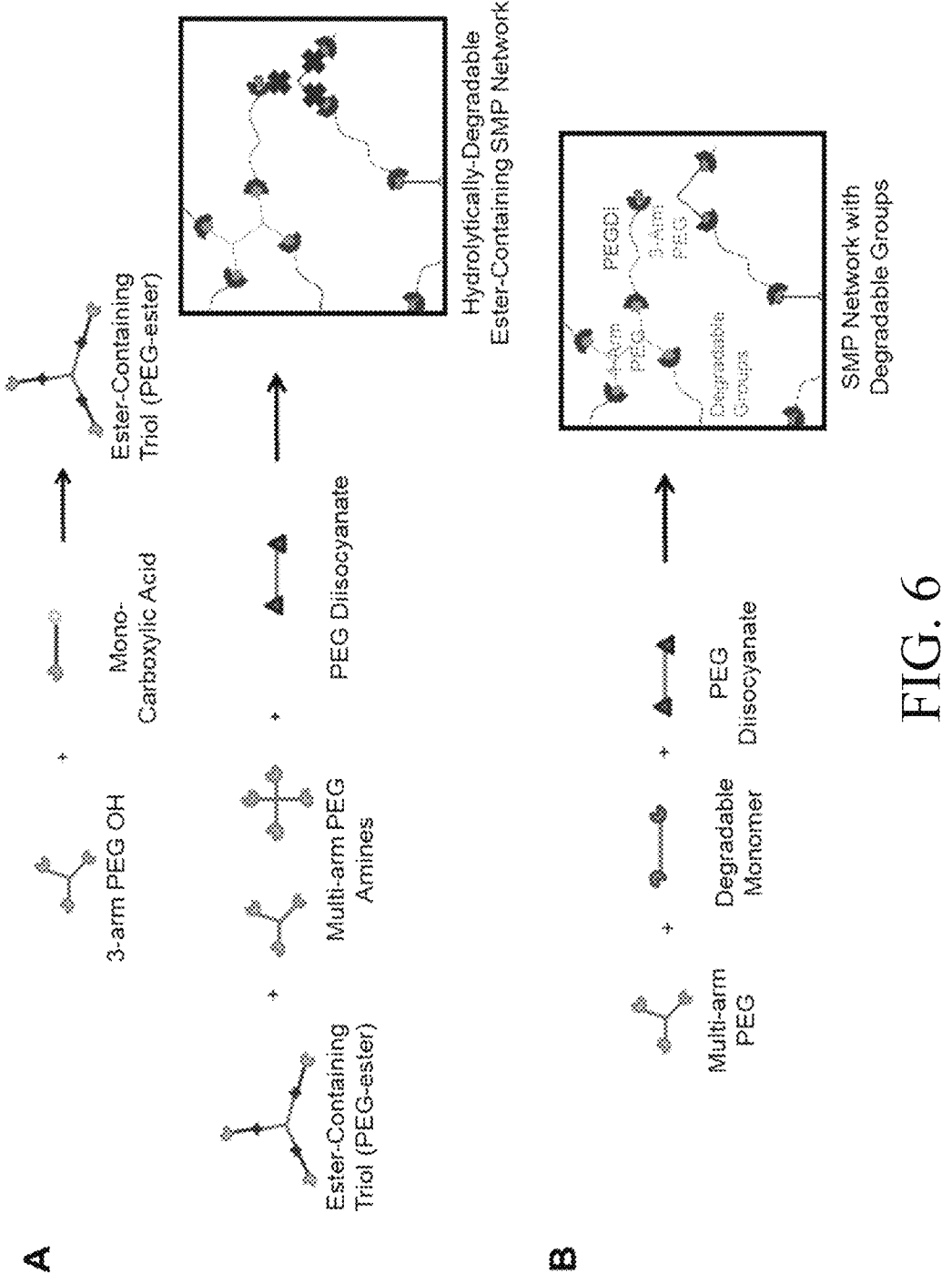
FIG. 6 is a schematic of a synthesis process for two potential routes of incorporating degradable linkages (A: incorporation of hydrolytically-degradable esters via prior esterification of foaming monomer and B: direct incorporation of bi-functional degradable monomer) into a shape memory polymer hydrogel wound scaffold according to the present invention.

To provide a degradable dressing, biodegradable groups can be incorporated into the foams using a number of routes. These include addition of hydrolytically-labile linkages using esterification of foaming monomers with mono-carboxylic acids, such as naturally occurring amino acids, as seen in FIG. 6. The mono-carboxylic acids will be selected to provide safe degradation byproducts that can be resorbed by the body. Another route is direct incorporation of a monomer that contains hydrolytically, oxidatively, or enzymatically degradable linkages, also shown in FIG. 6. The system can be designed to degrade within about 30 days in the wound environment so that dressing changes are not required.

The present invention thus provides a degradable SMP hydrogel foam to enhance treatment of chronic wounds. The fully synthetic system provides a cost-effective strategy that addresses some of the major concerns with chronic wound healing, including infection, moist healing, the need for a porous template for cell infiltration, and reduced risks of dressing changes.

Figure 7:
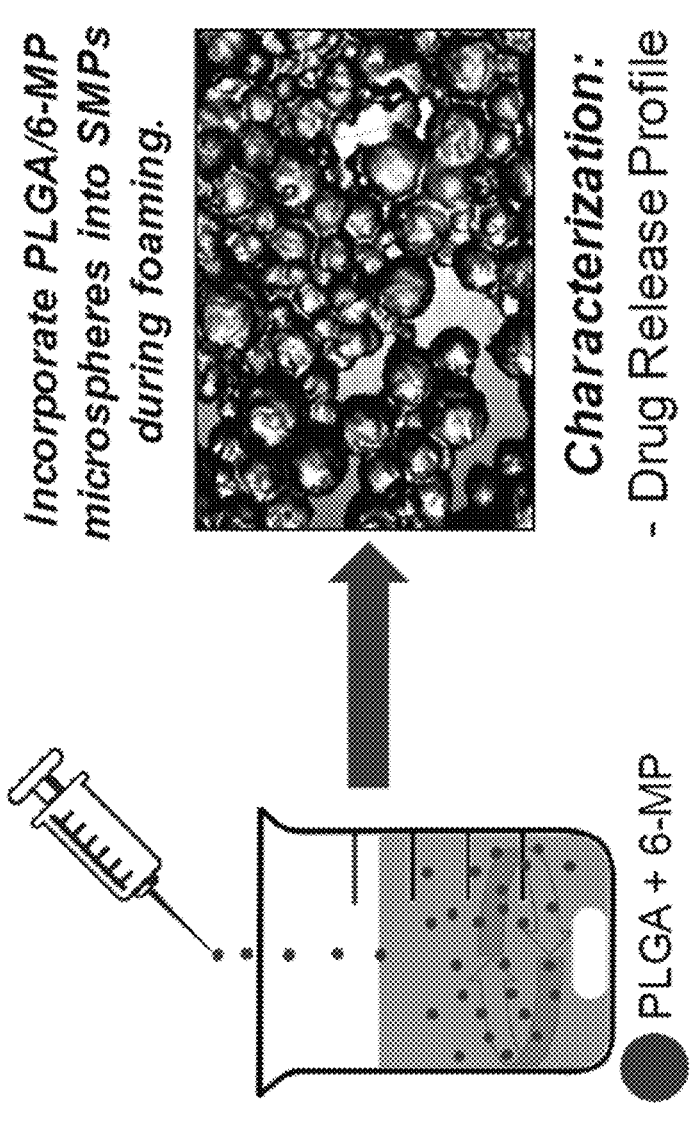
FIG. 7 is a schematic of a synthesis process for incorporation of drug containing microspheres.

As is shown in FIG. 7, a tunable drug delivery system can be incorporated by synthesizing immunosuppressant drug-containing microspheres into the foam. The microspheres will be incorporated into the SMP hydrogel foams at varied ratios.

Figure 8:
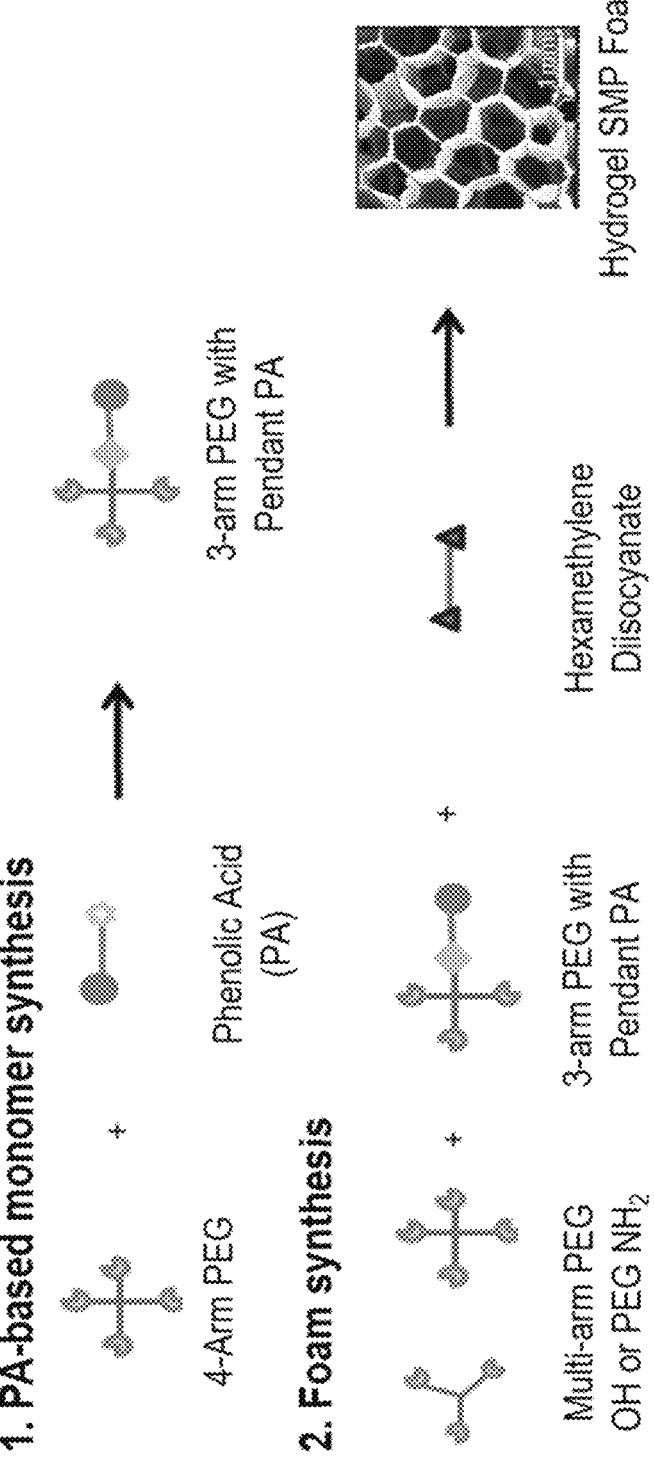
FIG. 8 is a schematic of an example synthesis processes for two potential routes of incorporation of a phenolic acid.

As shown in FIG. 8, phenolic acid-based monomers may be synthesized to form 3-arm PEG structures that may then be polymerized using a foaming process to form a hydrogel shape memory polymer foam. The monomers may be adapted for a particular usage by selecting the appropriate phenolic acid, adjusting multi-arm amine rations, and varying the PEG molecular weight. The resulting characteristics of swelling, pore size, thermal properties, shape recovery, cytocompatibility, antimicrobial activity, and antioxidant activity may thus be tailored.

Figure 9:
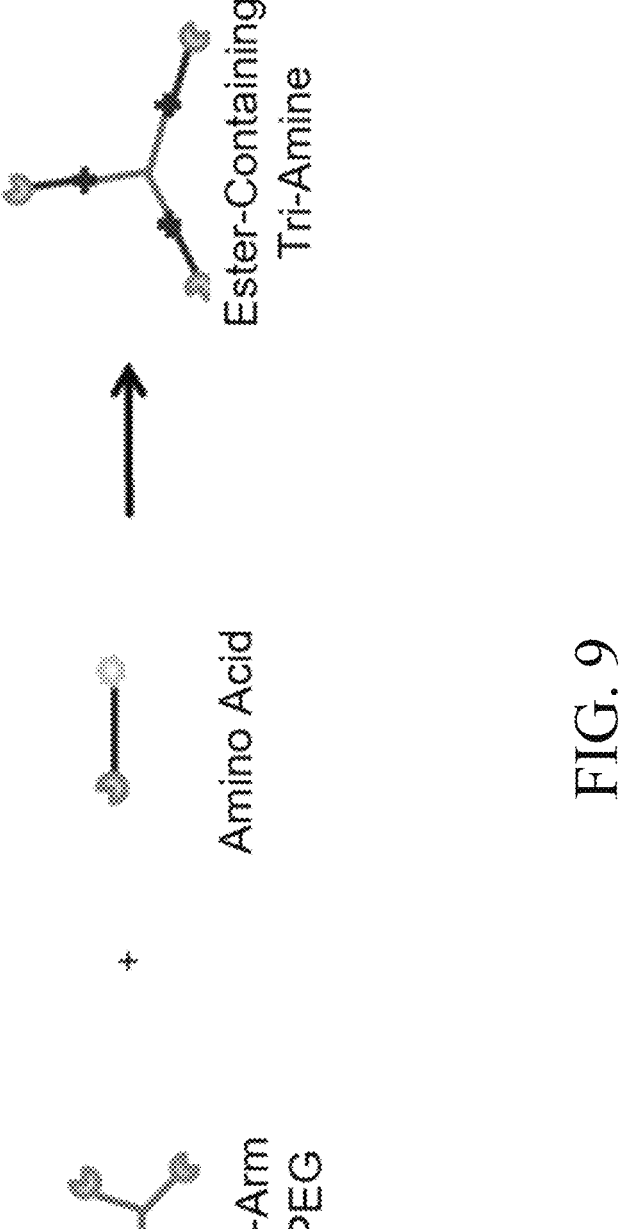
FIG. 9 is a schematic of an example of a synthesis process of incorporating degradable linkages.

As shown in FIG. 9, a 3-arm PEG monomer may be coupled to an amino acid to form an ester-containing tri-amine. This tri-amine may be used in place of 3-arm PEG during foam synthesis to form a degradable form.

Example 1

Multi-arm PEGs (hydroxyl (OH) or amine (NH2) end-groups) and PEG diisocyanates may be reacted together to form a hydrophilic, chemically crosslinked network, as seen in FIG. 4. The ratios of multi-arm PEGs (3 vs. 4 arms), PEG molecular weight, and endgroup chemistry may be systematically varied to synthesize libraries of bulk (solid) and foam (porous) hydrogels. The resulting scaffolds can be characterized in terms of physical, thermal, mechanical, and shape memory properties to establish structure-property relationships based upon monomer variables. Cytocompatibility of human dermal fibroblasts (HDFs) and human epidermal keratinocytes (HEKs) on SMPs may be assessed using conventional cytotoxicity models and approaches.

Referring to FIG. 6A, hydrolytically-degradable ester linkages may be formed by esterifying multi-arm PEG OH with a mono-carboxylic acid, such as glycine (an amino acid) to form degradable polyamines (triamine shown as example in FIG. 6A). Alternatively, an enzymatically degradable peptide sequence (e.g. GGGPQGIWGQGK) (SEQ ID NO: 1) could be directly incorporated via reactions between peptide amines and PEG diisocyanate. The resulting degradation profile (mass loss, morphology, and surface chemistry changes over time of incubation in degradative media) may be characterized for degradable SMPs according to the present invention. The cytocompatibility of scaffolds throughout the degradation process may also be quantified as described above. Following the successful completion of the above, SMP hydrogel efficacy may be assessed in healing in in vitro and in vivo models of normal and infected wounds.

Example 2

Bulk films may be composed of combinations of 2-arm and 3-arm poly(ethylene glycol), bis(2-hydroxyethyl ethylene diamine), sucrose, and hexamethylene diisocyanate. The resulting hydrogels exhibit shape memory around their melting points, high swelling (>200%) in water, and tunable melting points based upon gel chemistry (between 30 and 50° C.).

Example 3

Hydrogel foams may be composed of combinations of 2-arm and/or 3-arm poly(ethylene glycol) and 2-4 functional polyols and/or polyamines (e.g. N,N'bis(2 hydroxyethyl) ethylene diamine, 2-butyl-2-ethyl-1, 3-propanediol and/or 3-methyl-2, 5-pentane diol) with hexamethylene diisocyanate and/or diisocyanatobutane synthesized using porogen leaching with salt or paraffin beads of controlled sizes. Foams have swelling ratios of ~200% and tunable pore sizes and melting points (~20-40° C.).

Example 4

As seen FIG. 8, the antimicrobial compound can be a plant-based phenolic acid (PA). PAs exhibit broad antimicrobial properties, even against multi-drug resistant organisms and have antioxidant properties. Incorporated PAs could reduce infection risks and oxidative stress to enhance healing. PAs have efficacy against bacteria at concentrations that are feasible for incorporation into SMPs. The PA can be benzoic acid-based or cinnamic acid-based PAs. Other PAs for incorporation into SMP hydrogels to provide antioxidant and antimicrobial wound healing scaffolds can include but are not limited to vanillic, syringic, protocatechuic, p-coumaric, and ferulic acids.

PA-poly(ethylene glycol) (PEG) can be synthesized via an esterification reaction with 4-arm PEG OH to make a triol with a pendant phenolic acid using heat and a catalyst system such as 4-dimethylamino pyridine and dicyclohexylcarbodiimide. Multi-arm PEG hydroxyl (OH) or amine (NH2), PA-PEG, and hexamethylene diisocyanate can be reacted together using heat and mixing in the presence of surfactants, catalysts, and foam blowing agents to form a hydrophilic, chemically crosslinked foam. The ratios of multi-arm PEGS (3 vs. 4 arms), PEG molecular weight, PA-containing PEG concentration, and endgroup chemistry can be systematically varied to synthesize a library of porous foam hydrogels.

---

What is claimed is:

1. A porous wound scaffold, comprising;
   a shape memory polymer foam comprised of a cross-linked network of a multi-armed precursor having a plurality of hydroxyl end groups polymerized with a diisocyanate, wherein the multi-armed precursor is selected from group consisting of poly(ethylene glycol) and poly(vinyl alcohol); and
   an antimicrobial compound covalently coupled to at least one arm of the multi-armed precursor of the crosslinked network;
   wherein the shape memory polymer foam has a swelling ratio of at least 200 percent and will transition from a compressed geometry to an expanded geometry that is larger than the compressed geometry at a predetermined temperature.

2. The porous wound scaffold of claim 1, wherein the antimicrobial compound is pendant to the multi-armed precursor.

3. The porous wound scaffold of claim 1, wherein the antimicrobial compound is copolymerized with the multi-armed precursor.

4. The porous wound scaffold of claim 3, wherein the antimicrobial compound is a phenolic acid.

5. The porous wound scaffold of claim 4, wherein the predetermined temperature is below 37° C.

6. The porous wound scaffold of claim 5, wherein the shape memory polymer foam has an average of pore size of between 250 and 500 μm.

7. A porous wound scaffold, comprising;
   a shape memory polymer foam comprised of a cross-linked network of a multi-armed precursor having a plurality of hydroxyl end groups polymerized with a diisocyanate, wherein the multi-armed precursor is selected from group consisting of poly(ethylene glycol) and poly(vinyl alcohol); and
   a degradable compound covalently coupled to at least one arm of the multi-armed precursor of the crosslinked network;
   wherein the shape memory polymer foam has a swelling ratio of at least 200 percent and will transition from a compressed geometry to an expanded geometry that is larger than the compressed geometry at a predetermined temperature.

8. The porous wound scaffold of claim 7, wherein the degradable compound is pendant to the multi-armed precursor.

9. The porous wound scaffold of claim 7, wherein the degradable compound is copolymerized with the multi-armed precursor.

10. The porous wound scaffold of claim 7, wherein the degradable compound is SEQ ID NO: 1.

11. The porous wound scaffold of claim 10, wherein the transition temperature is below 37° C.

12. The porous wound scaffold of claim 11, wherein the shape memory polymer foam has an average of pore size of between 250 and 500 μm.

13. The porous wound scaffold of claim 12, further comprising a pharmaceutical drug incorporated into a plurality of microspheres that are suspended in the shape memory polymer foam.

14. A method of forming a shape memory polymer foam, comprising the steps:
   polymerizing a multi-armed precursor having a plurality of hydroxyl end groups with a diisocyanate to form a cross-linked network, wherein the multi-armed precursor is selected from group consisting of poly(ethylene glycol) and poly(vinyl alcohol) and wherein a compound that has antimicrobial properties or that is degradable is covalently bonded to at least one arm of the multi-armed precursor of the crosslinked network by a carboxylic acid of the multi-armed precursor or an isocyanate group of the diisocynate; and
   forming a plurality of pores when polymerizing the multi-armed precursor and the diisocyanate to produce a shape memory polymer foam that has a swelling ratio of at least 200 percent and will transition from a compressed second geometry to an expanded a primary geometry that is larger than the compressed geometry at a predetermined temperature.

15. The method of claim 14, wherein the step of forming plurality of pores comprises the steps of:
   polymerizing the multi-armed precursor that is bound to the compound in the presence of a plurality of particulates; and
   removing the plurality of particulates after polymerization.

16. The method of claim 15, wherein the plurality of particulates comprise salt and the step of removing the plurality of particulates comprising washing with an amount of water.

17. The method of claim 15, wherein the particulates comprise paraffin beads and the step of removing the plurality of particulates comprising washing with a solvent.

18. The method of claim 14, wherein the step of forming a plurality of pores comprises the step of blowing with a blowing agent selected from group consisting of water and a chemical blowing agent.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: enzymatically degradable peptide

<400> SEQUENCE: 1

Gly Gly Gly Pro Gln Gly Ile Trp Gly Gln Gly Lys
1               5                   10

---

7

8